United States Patent [19]

Cunkle et al.

[11] Patent Number: 6,080,864
[45] Date of Patent: Jun. 27, 2000

[54] DERIVATIVES OF 1-OXYL-4-HYDROXY-2,2,6,6-TETRAMETHYLPIPERIDINE

[75] Inventors: Glen T. Cunkle, Stamford; Matthew E. Gande, Danbury, both of Conn.; Raymond Seltzer, New City; Thomas F. Thompson, Highland Mills, both of N.Y.

[73] Assignee: Ciba Specialty Chemicals Corporation, Tarrytown, N.Y.

[21] Appl. No.: 09/241,485

[22] Filed: Feb. 1, 1999

Related U.S. Application Data

[60] Division of application No. 09/095,617, Jun. 10, 1998, Pat. No. 5,932,735, which is a continuation-in-part of application No. 08/876,014, Jun. 13, 1997, abandoned.

[51] Int. Cl.[7] .................................................. C07D 211/46
[52] U.S. Cl. ........................ 546/242; 546/220; 546/221; 546/222
[58] Field of Search ................................... 546/220, 221, 546/222, 242

[56] References Cited

U.S. PATENT DOCUMENTS

| | | | |
|---|---|---|---|
| 3,374,988 | 3/1968 | Bailey | 203/8 |
| 3,488,388 | 1/1970 | Altwicher et al. | 564/168 |
| 3,747,988 | 7/1973 | Bailey | 230/8 |
| 5,254,760 | 10/1993 | Winter et al. | 585/5 |
| 5,322,960 | 6/1994 | Sakamato et al. | 560/205 |
| 5,457,204 | 10/1995 | Steinmann | 546/242 |
| 5,496,875 | 3/1996 | Borzatta et al. | 524/99 |
| 5,504,243 | 4/1996 | Sakamato et al. | 560/205 |
| 5,877,344 | 3/1999 | Gande et al. | 560/205 |

FOREIGN PATENT DOCUMENTS

| | | |
|---|---|---|
| 0718168 | 4/1986 | European Pat. Off. . |
| 0697386 | 2/1996 | European Pat. Off. . |
| 0791573 | 8/1997 | European Pat. Off. . |
| 19510184 | 9/1996 | Germany . |
| 19609312 | 9/1997 | Germany . |
| 60-36501 | of 1985 | Japan . |
| 5320205 | 12/1993 | Japan . |
| 5320217 | 12/1993 | Japan . |
| 9268138 | 10/1997 | Japan . |
| 1127127 | 9/1968 | United Kingdom . |
| 98/02400 | 1/1998 | WIPO . |
| 98/56746 | 12/1998 | WIPO . |
| 99/05108 | 2/1999 | WIPO . |

OTHER PUBLICATIONS

Abstract for EP 0697386.
Abstract for DE 19609312.
Abstract for DE 19510184.
Chem. Abstr. 104:148699w (1986).
Ito et al. "Photochromic material" CA 119:238039, 1992.
Seltzer et al. "Inhibition of pulp and paper yellowing using nitroxides and other co–additives" CA 130:169756, 1999.
Rozantsev et al. "Synthesis of paramagnetic polymers" CA 68:69512, 1967.
Rozantsev et al. "New spin lbels and probes for biological studies" CA 79:105352, 1973.
Marinovic et al. "Study of matrix inhomogeneity of natural rubber and synthetic polyisoprenes by a spin probe method" CA 115:258067, 1991.
Wang et al. "Synthesis of spin–labelet anticancer derivatives of 5–fluorouracil" CA 119:117198, 1992.
Wang, Y. et al, Gaodeng Xuexiao Huaxue Xuebao, 1992, 13(12), pp. 1561–63, abstract only.

*Primary Examiner*—Ceila Chang
*Attorney, Agent, or Firm*—Luther A. R. Hall

[57] ABSTRACT

Selected derivatives of 1-oxyl-2,2,6,6-tetramethyl-4-hydroxypiperidine are surprisingly effective as inhibitors to prevent the premature polymerization of acrylic and methacrylic acids, their esters, their amides, vinyl acetate and acrylonitrile in the presence of water. Some of these derivatives are new compounds.

3 Claims, No Drawings

DERIVATIVES OF 1-OXYL-4-HYDROXY-2,2,6,6-TETRAMETHYLPIPERIDINE

This is a divisional of application Ser. No. 09/095,617, filed Jun. 10, 1998, now U.S. Pat. No. 5,932,735, which is a continuation-in-part of application Ser. No. 08/876,014, filed on Jun. 13, 1997, now abandoned.

The instant invention pertains to the use of selected derivatives of 1-oxyl-2,2,6,6-tetramethyl-4-hydroxypiperidineas inhibitors for preventing the premature polymerization of acrylic and methacrylic acids, their esters and amides, of vinyl acetate and of acrylonitrile in the presence of water.

BACKGROUND OF THE INVENTION

Many of the industrially important ethylenically unsaturated monomers are highly susceptible to unwanted radical polymerization initiated either thermally or by adventitious impurities. Some examples of these monomers are acrylic and methacrylic acid, acrylate and methacrylate esters, acrylamide and methacrylamide, vinyl acetate and acrylonitrile. Premature polymerization may occur during manufacture, purification or storage of the monomer. Many of these monomers are purified by distillation. It is in this operation where premature polymerization is most likely to occur and to be the most troublesome. Methods to prevent or reduce the amount of such polymerization are thus highly desirable since the prevention or mitigation of such premature polymerization increases the yield of purified monomer and also insures against costly and potentially dangerous runaway polymerization in the plant.

Stable nitroxides are known in the art to be effective in preventing the premature radical polymerization of ethylenically unsaturated monomers. Some examples are seen in Japanese Hei 9-268138 which discloses the stabilization of styrene by 1-oxyl-2,2,6,6-tetramethyl- 4-hydroxypiperidine and its lower alkyl ethers in the presence of nitrophenols. U.S. Pat. Nos. 3,747,988 describes the use of 1-oxyl-2,2,6,6-tetramethyl-4-hydroxypiperidine as a polymerization inhibitor for acrylonitrile in the presence of water and oxygen. U.S. Pat. No. 3,488,338 discloses that 1-oxyl-2,2,6,6-tetramethyl-4-hydroxypiperidine is an effective chain stopper in the aqueous polymerization of chloroprene. British Patent No. 1,127,127 describes the stabilization of neat acrylic acid by 1-oxyl-2,2,6,6-tetramethyl-4-hydroxypiperidine. Japanese Sho 60-36501 describes the stabilization of acrylate and methacrylate esters.

U.S. Pat. Nos. 5,322,960 and 5,504,243 disclose the use of 1-oxyl-2,2,6,6-tetramethyl-4-hydroxypiperidine in preventing the polymerization of acrylic and methacrylic acids and their esters in the presence of water, but tout the great advantages of using said oxyl compound in combination with manganese acetate, or with hydroquinone and phenothiazine.

EP 178,168 teaches the use of 1-oxyl-2,2,6,6-tetramethyl-4-hydroxypiperidine or its reaction product with hexamethylene diisocyanate in stabilizing acrylic acid or methacrylic acid in the presence of water.

EP 791,573 discloses that the lower alkyl or aryl esters of 1-oxyl-2,2,6,6-tetramethyl-4-hydroxypiperidine are effective polymerization inhibitors alone or in combination with various coadditives for vinyl acetate in the presence of water.

Japanese Hei 5-320205 generically describes the use of 1-oxyl-2,2,6,6-tetramethyl-4-hydroxypiperidine, its lower alkyl ethers and lower alkanoic esters in preventing the polymerization of acrylic and methacrylic acids alone, but preferably in the presence of chelating agents for ferric salts, such as ethylenediaminetetraacetic acid. The 4-hydroxy, 4-methoxy and 4-acetoxy derivatives are specifically disclosed.

Japanese Hei 5-320217 teaches the stabilization of acrylic and methacrylic acids with 1-oxyl-2,2,6,6-tetramethyl-4-hydroxypiperidine, its lower alkyl ethers and lower alkanoic esters alone, but preferably in the presence of phenothiazine, an aromatic amine or phenol. The 4-hydroxy, 4-methoxy and 4-acetoxy derivatives are specifically disclosed.

Since, during the processes to produce and purify various ethylenically unsaturated monomers, water is often present during one of the process steps, there is a long felt need for the stable nitroxide inhibitor to be sufficiently water soluble or miscible to remain homogeneous in wet monomer streams and to prevent polymerization in the aqueous phase and yet for the inhibitor to be able to partition to such an extent that it can prevent polymerization in both the aqeuous phase and in the organic monomer phase for inhibition protection throughout the entire process.

OBJECT OF THE INVENTION

The object of this invention is to provide a derivative of 1-oxyl-2,2,6,6-tetramethyl-4-hydroxypiperidine of sufficient water solubility and the concomitant ability to partition into an organic phase which will prevent the premature polymerization of ethylenically unsaturated monomers in the presence of water.

Another object of this invention to provide novel nitroxide compounds of value in stabilizing unsaturated monomers.

DETAILED DESCRIPTION

The instant invention is to a monomer composition stabilized against premature polymerization in the presence of water which comprises (A) an ethylenically unsaturated monomer which is an unsaturated acid, an unsaturated ester, an unsaturated amide, an unsaturated nitrile, unsaturated ether, vinyl pyridine, diethyl vinylphosphonate or sodium styrenesulfonate, and (B) an effective stabilizing amount of a compound of formula I, II, V or VI

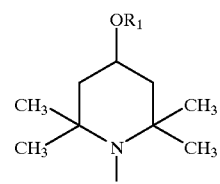

(I)

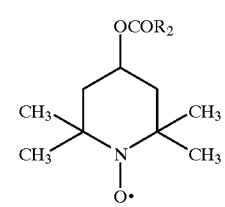

(II)

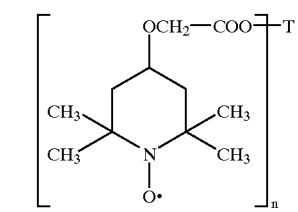

(V)

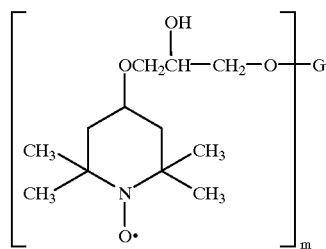

(VI)

wherein $R_1$ is alkenyl of 2 to 4 carbon atoms, propargyl, zlycidyl, alkyl of 2 to 6 carbon atoms interrupted by one or two oxygen atoms, substituted by one to three hydroxyl groups or both interrupted by said oxygen atoms and substituted by said hydroxyl groups, or $R_1$ is alkyl of 1 to 4 carbon atoms substituted by carboxy or by the alkali metal, ammonium or lower alkylammonium salts thereof; or $R_1$ is alkyl substituted by —COOE where E is methyl or ethyl, $R_2$ is alkyl of 3 to 5 carbon atoms interrupted by —COO— or by —CO, or $R_2$ is —CH$_2$(OCH$_2$CH$_2$)$_p$OCH$_3$ where p is 1 to 4; or $R_2$ is —NHR$_3$ where $R_3$ is alkyl of 1 to 4 carbon atoms, n is 2 to 4, when n is 2, T is —(CH$_2$CHR—O)$_q$CH$_2$CHR—, where q is 0 or 1, and R is hydrogen or methyl, when n is 3, T is glyceryl, when n is 4, T is neopentanetetrayl, m is 2 or 3, when m is 2, G is —(CH$_2$CHR—O)$_r$CH$_2$CHR—, where r is 0 to 3, and R is hydrogen or methyl, and when m is 3, G is glyceryl.

Preferably, $R_1$ is allyl, methallyl, glycidyl, 2,3-dihydroxypropyl, 2-hydroxy-4-oxapentyl or —CH$_2$COOH.

Preferably $R_2$ is methoxymethyl, 2-methoxyethoxymethyl, 2-(2-methoxyethoxy)ethoxymethyl, —CH$_2$COCH$_3$, —CH$_2$CH$_2$COOCH$_3$ or butylamino.

Preferably, n is 2, T is is —(CH$_2$CHR—O)$_q$CH$_2$CHR—, where q is 0, and R is hydrogen.

Preferably, m is 2, G is —(CH$_2$CHR—O)$_r$CH$_2$CHR—, where r is 0 or 1, and R is hydrogen.

The water contents of the instant compositions range from 0.1% to 99% by weight based on the total composition.

The monomers of component (A) have at least one carbon-carbon double bond capable of undergoing free radical induced polymerization. Such monomers are well-known in commerce and comprise a wide variety of structural types. Typical examples of such monomers are the unsaturated acids such as acrylic acid, methacrylic acid and crotonic acid; unsaturated esters such as the acrylates and methacrylates exemplified by butyl acrylate, methyl methacrylate, ethyl acrylate, methyl acrylate and vinyl acetate; unsaturated amides such as acrylamide and methacrylamide; unsaturated nitriles such as acrylonitrile and methacrylonitrile; unsaturated ethers such as methyl vinyl ether; and miscellaneous vinyl monomers such as the vinyl pyridines, diethyl vinylphosphonate and sodium styrenesulfonate.

Preferably the monomer is acrylic acid, methacrylic acid, butyl acrylate, ethyl acrylate, methyl methacrylate, vinyl acetate, acrylamide or acrylonitrile; most preferably acrylic acid, vinyl acetate or acrylonitrile; most especially acrylic acid.

The effective stabilizing amount of component (B) is 1 to 10000 ppm by weight based on the weight of monomer of component (A). Preferably, the amount of component (B) is 1 to 2000 ppm by weight based on the monomer of component (A). Most preferably, the amount of component (B) is 1 to 1000 ppm by weight based on the monomer of component (A).

The instant invention also pertains to novel compounds of formula III or formula

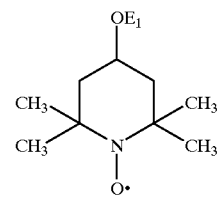

(III)

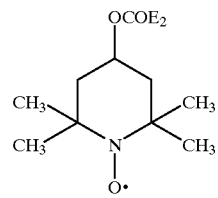

(IV)

wherein $E_1$ is alkyl of 2 to 6 carbon atoms interrupted by one or two oxygen atoms, substituted by two to three hydroxyl groups or both interrupted by said oxygen atoms and substituted by said hydroxyl groups, or $E_1$ is alkyl of 1 to 4 carbon atoms substituted by carboxy or by the alkali metal, ammonium or lower alkylammonium salts thereof; or $E_1$ is alkyl substituted by —COOE where E is methyl or ethyl, and $E_2$ is alkyl of 3 to 5 carbon atoms interrupted by —COO— or by —CO—, or $E_2$ is —CH$_2$(OCH$_2$CH$_2$)$_n$OCH$_3$ where n is 1 to 4; or $E_2$ is —NHE$_3$ where $E_3$ is alkyl of 1 to 4 carbon atoms, with the proviso that $E_1$ is not 2,3-dihydroxypropyl.

Preferably, $E_1$ is 2-hydroxy-4-oxapentyl or —CH$_2$COOH.

Preferably $E_2$ is methoxymethyl, 2-methoxyethoxymethyl, 2-(2-methoxyethoxy)ethoxymethyl, —CH$_2$COCH$_3$, —CH$_2$CH$_2$COOCH$_3$ or butylamino.

The intermediates needed to make the instant compounds are largely items of commerce.

The instant invention also pertains to a process for preventing the premature polymerization of an unsaturated monomer in the presence of water by incorporating therein an effective stabilizing amount of a compound of formula I or II described above.

The polymerization inhibitor ether or ester can be introduced into the monomer to be protected by any conventional method. It may be added just upstream of the point of desired application by any suitable means. In addition, this mixture may be injected separately into the distillation train along with the incoming feed of monomer or through separate entry points providing efficient distribution of the activated inhibitor mixture. Since the inhibitor is gradually depleted during operation, it is generally necessary to maintain the appropriate amount of the inhibitor ester in the distillation system by adding additional inhibitor during the course of the distillation process. Such addition may be carried out either on a continuous basis or by intermittently charging fresh inhibitor into the distillation system if the concentration of the inhibitor is to be maintained above the minimum required level.

The nitroxides of this invention are highly water compatible. As many of the processes needed to produce and purify the various ethylenically unsaturated monomers may have some water present during one of the process steps, it is important that the instant stable nitroxide inhibitor be sufficiently water soluble to prevent polymerization in the aqueous phase and yet for the inhibitor to be able to partition significantly into the organic monomer phase for inhibition protection throughout the entire process. Undesired premature polymerization must be limited or mitigated throughout the purification process to insure that the reactors, tanks and pipes used to make, store and transport the purified monomer remain free from high molecular weight polymeric material. The instant ether or ester inhibitors are tailored to have the desirable water compatibility properties needed to bring this about.

The amount of water present will depend on the specific monomer being stabilized. In the case of monomers of limited compatibility with water such as butyl acrylate, the water content will depend on the amount needed to saturate the ester, only a few percent. On the other hand with water miscible monomers such as acrylic acid, the amount of water possible theoretically much higher.

The following examples are meant to illustrate the instant invention and are not to be construed to limit the scope of the instant invention in any manner whatsoever.

EXAMPLE 1

1-Oxyl-2,2,6,6-Tetramethyl-4-Allyloxypiperidine

A vigorously stirred two phase solution of 30.0 g (0.17 mol) 1-oxyl-2,2,6,6-tetramethyl-4-hydroxypiperidine, 29.0 g (0.24 mol) of allyl bromide, 2.6 g (8 mmol) of tetrabutylammonium bromide, 100 mL of 50% aqueous sodium hydroxide and 30 mL of toluene is heated at 70° C. for 90 minutes. The mixture is partitioned between 100 mL of toluene, 100 mL of heptane and 200 mL of water. The organic phase is dried over anhydrous magnesium sulfate and concentrated to yield the title compound as a red oil after column chromatography.

EXAMPLE 2

1-Oxyl-2,2,6,6-Tetramethyl-4-(2-Methoxyethoxy) Piperidine

The title compound is synthesized using the same procedure as described in Example 1 and using 2-bromoethyl methyl ether in place of allyl bromide. The product is isolated as a red oil after column chromatography.

EXAMPLE 3

1-Oxyl-2,2,6,6-Tetramethyl-4-Glycidyloxypiperidine

The title compound is synthesized using the same general procedure as described in Example 1 and using epichlorohydrin in place of allyl bromide. The product is isolated as a low melting red solid after column chromatography.

EXAMPLE 4

1-Oxyl-2,2,6,6-Tetramethyl-4-(2,3-Dihydroxypropoxy)Piperidine 1.0 g of the compound of Example 3 is heated at 110° C. in 50 mL of 5% aqueous sodium hydroxide for six hours. The mixture is extracted with ethyl acetate, and the organic extract is dried and concentrated. The title compound is isolated as a red oil after column chromatography.

EXAMPLE 5

1-Oxyl-2,2,6,6-Tetramethyl-4-(2-Hydroxy-4-Oxapentoxy)Piperidine 1.0 g of the compound of Example 3 is heated at 60° C. in a solution of 0.25 g sodium methoxide in 50 mL of methanol for six hours. The reaction mixture is then partitioned between water and ethyl acetate. The title compound is isolated as a red oil after column chromatography.

EXAMPLE 6

1-Oxyl-2,2,6,6-Tetramethyl-4-(Carboethoxymethoxy)Piperidine 0.48 g (20 mmol) of sodium hydride is added to a solution of 3.0 g (17 mmol) of 1-oxyl-2,2,6,6-tetramethyl-4-hydroxypiperidine in 25 mL of anhydrous tetrahydrofuran. The reaction mixture is stirred under a blanket of nitrogen for one hour. The mixture is chilled to 0° C. and 2.9 g (17 mmol) of ethyl bromoacetate is added dropwise. After the addition is complete, the reaction is stirred for an additional 30 minutes during which time a white precipitate forms. The mixture is filtered and the solvent is removed under reduced pressure. The title compound is isolated as an orange solid after column chromatography and melts at 41–43° C.

EXAMPLE 7

1-Oxyl-2,2,6,6-Tetramethyl-4-(Carboxymethoxy) Piperidine 1.0 g (39 mmol) of the compound of Example 6 is added to a solution of 0.2 g sodium hydroxide in 20 mL of 1:1 water/methanol. The mixture is stirred for one hour, carefully acidified with 1% aqueous hydrogen chloride and then extracted with ethyl acetate. The organic extract is dried over anhydrous magnesium sulfate and then contenterated to afford the title compound as an orange solid.

EXAMPLE 8

1-Oxyl-2,2,6,6-Tetramethylpiperidin-4-yl 2-Methoxyethoxyacetate 34.4 grams of 1-oxyl-2,2,6,6-tetramethyl-4-hydroxypiperidine, 29.6 grams of methyl 2-methoxyethoxyacetate and 300 mL of heptane are transferred to a 500 mL 3-necked, round-bottomed flask equipped with a mechanical stirrer, Dean-Stark trap and condenser. Trace amounts of water are removed by azeotropic distillation. 0.25 mL of tetraisopropyl orthotitanate is added to the reaction mixture. The reaction mixture is refluxed for six hours and the liberated methanol is collected in the Dean-Stark trap. The reaction mixture is allowed to cool and is then partitioned between 300 mL of ethyl acetate and 300 mL of water. The phases are separated and the organic phase is washed with water and dried over anhydrous magnesium sulfate. Evaporation of the solvent leaves the title compound as a red oil.

EXAMPLE 9

1-Oxyl-2,2,6,6-Tetramethylpiperidin-4-yl 2-(2-Methoxyethoxy)Ethoxyacetate

The title compound is synthesized using the same procedure as described in Example 8 and using methyl 2-(2-methoxyethoxy)ethyoxyacetate in place of methyl 2-methoxyethoxyacetate. The title compound is isolated as a red oil after column chromatography.

EXAMPLE 10

1-Oxyl-2,2,6,6-Tetramethylpiperidin-4-yl Methoxyacetate

The title compound is synthesized using the same procedure as described in Example 8 and using methyl methoxyacetate in place of methyl 2-methoxyethoxyacetate. The title compound is isolated as an orange solid by crystallization from heptane and melts at 103° C.

EXAMPLE 11

1-Oxyl-2,2,6,6-Tetramethylpiperidin-4-yl Methyl Succinate

A solution of 6.0 g (35 mmol) of 1-oxyl-2,2,6,6-tetramethyl-4-hydroxypiperidine and 11.4 g (78 mmol) dimethyl succinate in 60 mL of heptane is brought to reflux. 0.05 mL of tetraisopropyl orthotitanate is added and the reaction mixture is refluxed for 16 hours while the evolved methanol is trapped in a Dean-Stark trap. The reaction mixture is then concentrated and the title compound is isolated as a red oil after column chromatography and melts at 76° C.

EXAMPLE 12

1-Oxyl-2,2,6,6-Tetramethylpiperidin-4-yl Acetoacetate

The title compound is synthesized using the same procedure as described in Example 11 but using methyl acetoacetate in place of dimethyl succinate. The title compound is isolated as a red oil after column chromatography.

EXAMPLE 13

1-Oxyl-2,2,6,6-Tetramethyl-Piperidin-4-yl Butylcarbamate 0.1 g of di-n-butyltin dilaurate is added to a solution of 1.0 g (5.8 mmol) of 1-oxyl-2,2,6,6-tetramethyl-4-hydroxypiperidine and 0.58 g (5.8 mmol) of butyl isocyanate in 10 mL of carbon tetrachloride. After stirring for four hours at ambient temperature, the solution is concentrated and the title compound is isolated as a red oil after column chromatography.

In the Examples two different test methods are employed to determine the effectiveness of the nitroxide esters as inhibitors. The method is chosen to simulate different aspects of the purification processes.

Method 1

Acrylic acid is distilled to remove any storage stabilizer present. Stock stabilizer solutions (1.5 mg/mL) are prepared in propionic acid. This stock solution is added to the distilled acrylic acid to give a test solution having 5 ppm of total stabilizer. Aliquots of this test solution are then placed into three separate reaction tubes. Each tube is purged with a gas mixture (0.65% oxygen in nitrogen) for ten minutes. The tubes are then sealed and placed in a 110° C. oil bath. The tubes are watched till the appearance of visible polymer formation is observed as a precipitate. Failure times are reported as an average of at least three tubes.

Method 2

Test solutions are prepared as in Method 1 except that the stock stabilizer solution is prepared at 0.75 mg/mL giving a test solution with 2.5 ppm of total stabilizer. Aliquots (1 mL) of the test solution are placed into three separate reaction tubes. To each tube is added 0.5 mL of toluene and 0.5 mL of distilled water. Each tube is purged as described in Method 1 and then sealed. The tubes are placed in a 90° C. oil bath and heated till visible polymer is observed as a precipitate. Failure times are reported as an average of at least three tubes.

EXAMPLE 18

Following the procedure of Method 1, it is seen that water miscible nitroxides and hydrophobic nitroxides each perform similarly in neat acrylic acid in the absence of water.

TABLE 1

Stabilization of Neat Acrylic Acid

| Compound* of Example (5 ppm by weight) | Time to Onset of Polymerization (minutes) |
|---|---|
| none | 5 |
| A | 220 |
| Example 8 | 220 |

*A is bis(1-oxyl-2,2,6,6-tetramethylpiperidin-4-yl) sebacate.

Each of the nitroxide compounds provide nearly the same stabilization efficacy to neat acrylic acid.

EXAMPLE 19

Following the procedure of Method 2 where water is present in the acrylic acid, there is a clear difference in the superior stabilization performance of the instant water compatible nitroxides of formula I or formula II compared to the hydrophobic nitroxides as seen in Table 2.

TABLE 2

Stabilization of Aqueous Acrylic Acid

| Compound* of Example (5 ppm by weight) | Time to Onset of Polymerization (minutes) |
|---|---|
| none | 30 |
| A | 240 |
| B | 130 |
| Example 1 | 250 |
| Example 2 | 350 |
| Example 3 | 490 |
| Example 4 | 320 |
| Example 5 | 350 |
| Example 6 | 400 |
| Example 7 | 230 |
| Example 8 | 325 |

TABLE 2-continued

Stabilization of Aqueous Acrylic Acid

| Compound* of Example (5 ppm by weight) | Time to Onset of Polymerization (minutes) |
|---|---|
| Example 9 | 520 |
| Example 10 | 645 |
| Example 11 | 600 |
| Example 13 | 410 |

*A is bis(1-oxyl-2,2,6,6-tetramethylpiperidin-4-yl) sebacate.
B is 1-oxyl-2,2,6,6-tetramethylpiperidin-4-yl octanoate.

What is claimed is:

1. A compound of formula III

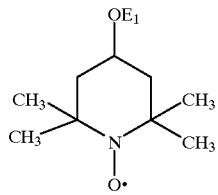 (III)

where $E_1$ is 2-hydroxy-4-oxapentyl or —$CH_2COOH$.

2. A compound of formula IV

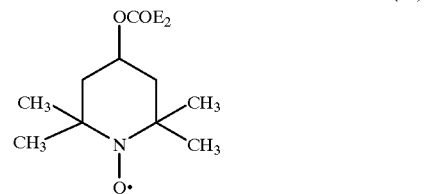 (IV)

where $E_2$ is methoxymethyl, 2-methoxyethoxymethyl, 2-(2-methoxyethoxy)ethoxymethyl, —$CH_2COCH_3$, —$CH_2CH_2COOCH_3$ or butylamino.

3. A compound according to claim 2 of which is 1-oxyl-2,2,6,6-tetramethyl-piperidin-4-yl 2-(2-methoxyethoxy)ethoxyacetate, 1-oxyl-2,2,6,6-tetramethyl-piperidin-4-yl methoxyacetate or 1-oxyl-2,2,6,6-tetramethylpiperidin-4-yl methyl succinate.

* * * * *